US011260375B2

(12) United States Patent
Berweiler et al.

(10) Patent No.: US 11,260,375 B2
(45) Date of Patent: Mar. 1, 2022

(54) PROCESS AND CATALYST FOR PREPARING 1,4-BUTANEDIOL

(71) Applicant: EVONIK OPERATIONS GMBH, Essen (DE)

(72) Inventors: Monika Berweiler, Maintal (DE); Markus Göttlinger, Rodenbach (DE); Meike Roos, Büdingen (DE); Matthias Schwarz, Flieden (DE); René Poss, Karlsruhe (DE)

(73) Assignee: Evonik Operations GmbH, Essen (DE)

( * ) Notice: Subject to any disclaimer, the term of this patent is extended or adjusted under 35 U.S.C. 154(b) by 75 days.

(21) Appl. No.: 16/338,015

(22) PCT Filed: Sep. 27, 2017

(86) PCT No.: PCT/EP2017/074528
§ 371 (c)(1),
(2) Date: Mar. 29, 2019

(87) PCT Pub. No.: WO2018/060269
PCT Pub. Date: Apr. 5, 2018

(65) Prior Publication Data
US 2019/0232256 A1 Aug. 1, 2019

(30) Foreign Application Priority Data
Sep. 30, 2016 (EP) .................................. 16191735

(51) Int. Cl.
| *B01J 23/755* | (2006.01) |
| *B01J 25/02* | (2006.01) |
| *B01J 35/02* | (2006.01) |
| *B01J 35/04* | (2006.01) |
| *B01J 35/10* | (2006.01) |
| *C07C 29/17* | (2006.01) |
| *B01J 37/00* | (2006.01) |
| *B01J 37/08* | (2006.01) |
| *B01J 37/02* | (2006.01) |
| *B01J 23/26* | (2006.01) |
| *B01J 23/28* | (2006.01) |
| *B01J 23/745* | (2006.01) |
| *C07C 31/20* | (2006.01) |

(52) U.S. Cl.
CPC ............. *B01J 25/02* (2013.01); *B01J 23/755* (2013.01); *B01J 35/023* (2013.01); *B01J 35/026* (2013.01); *B01J 35/04* (2013.01); *B01J 35/1076* (2013.01); *B01J 37/0018* (2013.01); *B01J 37/0063* (2013.01); *C07C 29/172* (2013.01); *B01J 23/26* (2013.01); *B01J 23/28* (2013.01); *B01J 23/745* (2013.01); *B01J 37/0215* (2013.01); *B01J 37/0217* (2013.01); *B01J 37/0225* (2013.01); *B01J 37/08* (2013.01); *C07C 31/207* (2013.01)

(58) Field of Classification Search
CPC ........ B01J 25/02; B01J 23/755; B01J 35/023; B01J 35/026; B01J 35/04; B01J 35/1076; C07C 29/172
See application file for complete search history.

(56) References Cited

U.S. PATENT DOCUMENTS

| 1,628,190 | A | | 5/1927 | Raney | |
| 1,915,473 | A | | 6/1933 | Raney | |
| 2,139,602 | A | | 12/1938 | Raney | |
| 2,895,819 | A | * | 7/1959 | Fiedler | ..................... C22C 1/08 502/335 |
| 2,967,893 | A | | 1/1961 | Hort et al. | |
| 2,977,327 | A | | 3/1961 | Raney | |
| 4,049,580 | A | | 9/1977 | Oden et al. | |
| 5,399,793 | A | | 3/1995 | Vargas et al. | |
| 6,262,317 | B1 | * | 7/2001 | Becker | ..................... B01J 8/025 568/861 |
| 6,399,793 | B1 | | 6/2002 | Kronenthal et al. | |
| 6,969,780 | B1 | | 11/2005 | Dubner et al. | |
| 7,524,996 | B2 | * | 4/2009 | Lorenz | ..................... C07C 29/17 568/856 |
| 7,538,254 | B2 | * | 5/2009 | Lorenz | ..................... C07C 29/17 568/856 |
| 7,572,941 | B2 | * | 8/2009 | Lorenz | ..................... C07C 29/17 568/856 |
| 7,605,292 | B2 | * | 10/2009 | Lorenz | ..................... C07C 29/17 568/856 |
| 7,612,241 | B1 | | 11/2009 | White et al. | |

(Continued)

FOREIGN PATENT DOCUMENTS

| CA | 2 823 676 | 8/2012 |
| DE | 102 45 510 | 4/2004 |

(Continued)

OTHER PUBLICATIONS

International Search Report for PCT/EP2019/053236 (international counterpart of copending U.S. Appl. No. 16/969,607), filed Feb. 11, 2019.

(Continued)

*Primary Examiner* — Cam N. Nguyen
(74) *Attorney, Agent, or Firm* — Law Office of: Michael A. Sanzo, LLC

(57) ABSTRACT

The present invention relates to a process for preparing 1,4-butanediol (BDO) by hydrogenating 2-butyne-1,4-diol (BYD) or 4-hydroxybutanal (4-HBA) in the presence of a catalyst of the Raney type having a porous foam structure, wherein the macroscopic pores have sizes in the range of 100 to 5000 μm, and a bulk density of up to 0.8 kg/L.

20 Claims, No Drawings

(56) References Cited

U.S. PATENT DOCUMENTS

| | | | |
|---|---|---|---|
| 9,029,290 B2* | 5/2015 | Lee | B82Y 30/00 502/402 |
| 9,346,079 B2* | 5/2016 | Lee | B01J 20/3078 |
| 9,567,276 B2 | 2/2017 | Klasovsky et al. | |
| 9,598,537 B2 | 3/2017 | Roos et al. | |
| 9,943,818 B2* | 4/2018 | Jin | B01J 7/02 |
| 2002/0151751 A1* | 10/2002 | Ostgard | B01J 25/02 564/420 |
| 2002/0193618 A1* | 12/2002 | Ostgard | C07C 29/17 554/141 |
| 2003/0047505 A1 | 3/2003 | Grimes et al. | |
| 2004/0199019 A1 | 10/2004 | Schmidt | |
| 2011/0011772 A1 | 1/2011 | Schmidt | |
| 2012/0154983 A1* | 6/2012 | Zhang | C22C 26/00 361/502 |
| 2014/0038816 A1* | 2/2014 | Bakker | B01J 20/06 502/337 |
| 2014/0221700 A1 | 8/2014 | Radivojevic | |
| 2018/0230081 A1 | 8/2018 | Rüfer et al. | |
| 2019/0210010 A1 | 7/2019 | Pinkos et al. | |
| 2019/0232257 A1 | 8/2019 | Weiland | |
| 2019/0344248 A1 | 11/2019 | Pinkos et al. | |
| 2020/0016579 A1 | 1/2020 | Schreiber et al. | |
| 2020/0016583 A1 | 1/2020 | Merkel et al. | |
| 2021/0032185 A1 | 2/2021 | Roos et al. | |

FOREIGN PATENT DOCUMENTS

| | | |
|---|---|---|
| EP | 0 340 970 | 11/1989 |
| EP | 0 807 464 | 11/1997 |
| EP | 2 764 916 | 8/2014 |
| EP | 3 115 106 | 1/2017 |
| GB | 1 242 358 | 8/1971 |
| WO | WO 02/055453 | 7/2002 |
| WO | WO 2005/039764 | 5/2005 |
| WO | WO 2007/028411 | 3/2007 |
| WO | WO 2008/151614 | 12/2008 |
| WO | WO 2018/060245 | 4/2018 |
| WO | WO 2021/058702 | 4/2021 |
| WO | WO 2021/058703 | 4/2021 |
| WO | WO 2021/058704 | 4/2021 |
| WO | WO 2021/058705 | 4/2021 |
| WO | WO 2021/058706 | 4/2021 |
| WO | WO 2021/058719 | 4/2021 |

OTHER PUBLICATIONS

Written Opinion of the International Searching Authority for PCT/EP2019/053236 (international counterpart of copending U.S. Appl. No. 16/969,607), filed Feb. 11, 2019.
Haibin, et al., "Polymer-supported catalysts for clean preparation of n-butanol," Catalysis Science & Technology 4(8):2499-2503 (May 2014).
Petró, et al., "A new alumina-supported, not pyrophoric Raney-type Ni-catalyst," Applied Catalysis A: General 190:73-86.
Ullman's Encyclopedia of Industrial Chemistry, "Metal Foams" chapter, publisned online on Jul. 15, 2012, DOI: 25 10.1002/14356007.c16_c01.pub2.
U.S. Appl. No. 16/969,607, filed Aug. 13, 2020, Roos.
International Search Report for corresponding PCT/EP2017/074528 filed Sep. 27, 2017.
Written Opinion of the International Searching Authority for corresponding PCT/EP2017/074528 filed Sep. 27, 2017.
International Preliminary Report on Patentability for corresponding PCT/EP2017/074528 filed Sep. 27, 2017.
European Search Report and Search Opinion for corresponding EP 16 19 1735 filed Sep. 30, 2016.
International Search Report for PCT/EP2017/074491 (international counterpart of copending U.S. Appl. No. 16/338,044), filed Sep. 27, 2017.
Written Opinion of the International Searching Authority for PCT/EP2017/074491 (international counterpart of copending U.S. Appl. No. 16/338,044), filed Sep. 27, 2017.
International Preliminary Report on Patentability for PCT/EP2017/074491 (international counterpart of copending U.S. Appl. No. 16/338,044), filed Sep. 27, 2017.
European Search Report and Search Opinion for EP 16 19 1751 international counterpart of copending U.S. Appl. No. 16/338,044, filed Sep. 30, 2016.
Abdullah, et al., "The use of bulk density measurments as flowability indicators," Powder Technology 102(2):151-165 (May 1999).
Brunauer, et al., "Adsorption of Gases in Multimolecular Layers," J. Am. Chem. Soc. 60:309-319 (Feb. 1938).
Brunet Espinosa, "Ni in CNFs: Highly Active for Nitrate Hydrogenation," ACS Catalysis 6:5432-5440 (2016).
Coleman, et al., "Evaluation of Foam Nickel for the Catalytic Partial Oxidation of Methane," Catalysis Letters 128(1-2):144-153 (Nov. 2008).
Kolaczkowski, et al., "Potential for metal foams to act as structured catalysy supports in fixed-bed reactors," CatalysisToday 273:221-233 (2016).
Li, et al., "Ni-$Al_2O_3$/Ni-Foam Catalyst with Enhanced Heat Transfer for Hydrogenation of $CO_2$ to Methane," AIChE Journal 61(12):4323-4331 (Dec. 2015).
Liu, et al., :Monolithic catalysts with Pd deposited on a structured nickel foam packing, Catalysis Today 273:34-40 (Apr. 2016).
U.S. Appl. No. 16/338,044, filed Mar. 29, 2019, Wieland.
Office Action dated Mar. 9, 2020 for copending U.S. Appl. No. 16/338,044.
Luther, E. et al., "Nonostructured Metal Foams: Synthesis and Applications," PowderMet2009, Las Vegas, NV, Los Alamos National Laboratory, 12 pages (2009).
Office Action dated Sep. 18, 2019 for copending U.S. Appl. No. 16/338,044.
Response to Office Action filed Jan. 8, 2020 for copending U.S. Appl. No. 16/338,044.
Response to Office Action for copending U.S. Appl. No. 16/338,044, filed Aug. 9, 2020.
International Preliminary Report on Patentability for PCT/EP2019/053236 (international counterpart of copending U.S. Appl. No. 16/969,607), filed Feb. 11, 2019.
European Search Report and Search Opinion for EP 18 15 6599 (European counterpart of copending U.S. Appl. No. 16/969,607), filed Feb. 14, 2018, with English language machine translation of the Search Opinion attached.
English language machine translation of the European Search Opinion for corresponding EP 16 19 1735, filed Sep. 30, 2016.
English language machine translation of the European Search Opinion for for EP 16 19 1751 international counterpart of copending U.S. Appl. No. 16/338,044, filed Sep. 30, 2016.
Ullmann's Encyclopedia of Industrial Chemistry: G. Eigenberger, W. Ruppel: "Catalytic Fixed-Bed Reactors", Wiley-VCH, online ISBN: 9783527306732 | DOI: 10.1002/14356007; 2012).
Ullmann's Encyclopedia of Industrial Chemistry: D. Sanfilippo, P.N. Rylander: "Hydrogenation and Dehydrogenation", Wiley-VCH, online ISBN: 9783527306732 | DOI: 10.1002/14356007; 2012).
Notice of Allowance dated Sep. 28, 2020, for copending U.S. Appl. No. 16/338,044.
International Search Report for PCT/EP2020/076823 (international counterpart of copending U.S. Appl. No. 17/059,448), filed Sep. 25, 2020.
Written Opinion of the International Searching Authority for PCT/EP2020/076823 (international counterpart of copending U.S. Appl. No. 17/059,448), filed Sep. 25, 2020.
Request for Continued Examination filed Dec. 25, 2020, for copending U.S. Appl. No. 16/338,044.
Notice of Allowance dated Apr. 19, 2021, for copending U.S. Appl. No. 16/338,044.
U.S. Appl. No. 17/053,340, filed Nov. 5, 2020.
U.S. Appl. No. 17/059,448, filed Nov. 29, 2020.
Request for Continued Examination for copending U.S. Appl. No. 16/969,607, filed Jan. 11, 2022.

(56) References Cited

OTHER PUBLICATIONS

Notice of Allowance for copending U.S. Appl. No. 16/969,607, dated Jan. 4, 2022.

* cited by examiner

PROCESS AND CATALYST FOR PREPARING 1,4-BUTANEDIOL

CROSS REFERENCE TO RELATED APPLICATIONS

The present application is US national stage of international application PCT/EP2017/074528, which had an international filing date of Sep. 27, 2017, and which was published on Apr. 5, 2018. Priority is claimed to European application EP 16191735.6, filed on Sep. 30, 2016.

The present invention relates to a process for preparing 1,4-butanediol (BDO) and a catalyst for use in this process.

1,4-Butanediol itself is used especially in the textile, leather, food and pharmaceutical industries. As an intermediate, it is used mainly for the preparation of thermoplastic polyesters. In addition, BDO is a synthetic precursor in the production of some important chemical intermediates and solvents such as tetrahydrofuran (THF), γ-butyrolactone or pyrrolidine.

The industrial processes most frequently used for producing BDO are based on a continuous hydrogenation of 2-butyne-1,4-diol (BYD) catalysed by modified nickel catalysts. A one-stage variant of this process is typically carried out at 80-160° C. at a pressure of approximately 300 bar in a fixed bed reactor. A two-stage hydrogenation of BYD is also known, wherein the first stage, in which mainly 2-butene-1,4-diol (BED) is produced, is carried out at a lower pressure of approximately 40 bar. In the second stage BED is converted at 300 bar to give BDO. In addition, other processes for producing BDO are known based on acetylene as main raw material. For instance, allyl alcohol can be converted to 4-hydroxybutanal (4-HBA) by hydroformylation with synthesis gas ($CO+H_2$) and be further hydrogenated to give BDO, in which both steps may also take place simultaneously. Further information regarding BDO is described, for example, in Ullmann's Encyclopedia of Industrial Chemistry, Chapter "Butanediols, Butenediol and Butynediol" published online on 15.06.2000, DOI: 10.1002/14356007.a04_455.

The nickel catalysts of the "Raney type" frequently used for the hydrogenation are generally prepared by forming an at least binary metal alloy, usually comprising aluminium (Al) and nickel (Ni), and subsequently leaching out aluminium. Descriptions of such processes are disclosed for example in the publications U.S. Pat. Nos. 1,628,190 A, 1,915,473 A, 2,139,602, 2,977,327.

U.S. Pat. No. 2,967,893 A discloses the use of a slurry of a pulverulent nickel catalyst modified with copper as promoter for hydrogenating BYD to BDO.

The activation of a precursor of the catalyst can take place separately or in situ in a hydrogenation reactor for producing BDO, as described in EP 0340970 A2 and DE 2004611 A1 for example.

DE 2004611 A discloses a continuous process for producing BDO by hydrogenating an aqueous solution of BYD. A fixed-bed of a granular nickel-aluminium catalyst having openings is used, which has been activated by removing approximately 5 to 30% of the aluminium from a nickel-aluminium alloy consisting of predominantly approximately 35 to 60% by weight nickel and approximately 40 to 65% by weight aluminium. The catalyst particles forming the fixed bed have particle sizes in the range of approximately 2 cm to 1.4 mm, preferably of approximately 1 cm to 2 mm.

EP 0807464 A1 discloses a process for the catalytic hydrogenation of hydroxyaldehydes and cyclic hydroxyethers over a modified Raney nickel catalyst comprising 40-98% by weight Ni, 1-50% by weight Al, 0.05-15% by weight Fe and optionally 0.05-10% by weight of at least one metal selected from the group consisting of Cr, Mo, W, Co, Mn and Ti. This catalyst can be of the powder type if the reaction is carried out in a slurry bed reactor. The catalyst disclosed in EP 0807464 A1 can also be of the granular type if the reaction is carried out in a fixed bed reactor such as in DE 2004611 A.

EP 1833778 B1 discloses a process for hydrogenating 4-hydroxybutyraldehyde (HBA) to 1,4-butanediol (BDO) and/or 2-methyl-3-hydroxypropionaldehyde (HMPA) to 2-methyl-1,3-propandiol, wherein an aqueous solution of HBA and/or HMPA is contacted with hydrogen in an adiabatic hydrogenation zone, by contact with a fixed bed of a hydrogenation catalyst which is a nickel catalyst activated with molybdenum.

The disadvantage of the processes known to date for producing BDO in industrial applications is the extremely high demand for nickel, which is used as hydrogenation catalyst of the Raney type in these processes. As described above, nickel catalysts of the granular type are typically used in continuous processes, which are introduced into the reactor as non-activated precursors and are activated in situ by leaching out of aluminium. These catalysts typically have bulk densities of more than 1.5 kg/L, such that in filling reactors of 5 to 50 m$^3$ with catalyst, as required in the case of the 2.0 customary activity of these catalysts to achieve sufficient product yields, between 8 and 100 tonnes of nickel are used.

With a mass fraction of around 0.01% in the earth's shell, nickel is one of the more rare metals. The availability in economically viable amounts is limited. In addition, the worldwide demand for nickel for industrial applications is constantly increasing, for example in the electronics and materials sector.

The object of the present invention was therefore to provide an economic, and particularly with regard to the nickel demand, maximally resource-conserving process for the catalytic preparation of 1,4-butanediol. A further object was to provide catalysts by means of which the appropriate chemical reactions to give BDO can be conducted with adequate yields and selectivities under industrially relevant process conditions.

These objects are achieved by a process for preparing 1,4-butanediol by hydrogenating 2-butyne-1,4-diol or 4-hydroxybutanal, wherein an aqueous solution comprising 2-butyne-1,4-diol or 4-hydroxybutanal is brought into contact with hydrogen and an activated nickel catalyst having a porous foam structure, wherein the macroscopic pores have sizes in the range of 100 to 5000 μm, and a bulk density of not more than 0.8 kg/L.

The process according to the invention is conducted in the presence of water. Preferably, 1 to 70% by weight aqueous solutions of BYD or 4-HBA are used as reactant. Depending on the reactor concept and procedure, the reactant solutions brought into contact with the activated nickel catalyst can comprise up to 60% by weight of the BDO target product. This applies particularly if the hydrogenation reactors in which the process according to the invention is carried out are loop reactors.

The process according to the invention is preferably carried out at a hydrogen pressure in the range of 10 to 350 bar. Here, the hydrogenation of 4-HBA is preferably carried out at 10 to 110 bar, particularly preferably 40 to 100 bar. The hydrogenation of BYD to BDO is preferably carried out at a hydrogen pressure in the range from 50 to 350 bar, particularly preferably from 75 to 320 bar, and especially preferably from 100 to 300 bar.

The process according to the invention can be carried out at temperatures of 50° C. to 250° C. The hydrogenation of 4-HBA to BDO is preferably carried out at 50 to 200° C., particularly preferably at 50 to 150° C. and especially preferably in the temperature range of 50 to 100° C. The hydrogenation of BYD to BDO is preferably carried out in a temperature range of 50 to 150° C., particularly preferably at 70 to 140° C. and especially preferably in the temperature range from 80 to 135° C. The process according to the invention for hydrogenating BYD or 4-HBA can be carried out batchwise or continuously. In the case of batchwise operation (set operation) in a stirred tank reactor, the catalyst used can be stirred in loose form in the reaction mixture. After completion of the reaction, the catalyst can be separated from the reaction mixture, e.g. by filtration, drawing off/pumping off the supernatant reaction solution or in another manner known to those skilled in the art.

A holding device is preferably used for the catalyst used. If the process according to the invention is carried out batchwise in a stirred tank reactor, the catalyst is preferably arranged in a holding device close to the stirrer shaft such that a flow of the reaction mixture through the catalyst bed inserted in the holding device is generated by the stirrer. This embodiment has the advantage, compared to the loose, i.e. non-fixed use of the catalyst, that a subsequent separation of the product mixture from the catalyst in an additional process step is not required.

The process according to the invention is preferably carried out continuously in a fixed bed reactor, for example in a trickle bed reactor or liquid-filled reactor, in a bubble column or in another reactor type known in the art. All these reactor types can be operated in a "once through" mode, in which the reactants (feed) are introduced into the reactor and the product mixture is removed after the reaction. Alternatively, a portion of the product mixture from the reactor can be passed back into the reaction zone (circulation stream). In such a circulation regime (recycling mode), the weight ratio of feed to circulation stream is 0.025 to 0.25, preferably 0.05 to 0.15, particularly preferably 0.05 to 0.1.

The conversion of BYD to BDO can be carried out in one stage or two stages.

The one-stage reaction regime of the hydrogenation of BYD to BDO is preferably carried out continuously, wherein the catalyst is present as a fixed bed in an adiabatically operated reactor.

The temperature in the reactor inlet is then preferably in the range of 80 to 100° C., the temperature in the reactor outlet between 110-150° C. In this case, a temperature in the reaction zone, in which the hydrogenation reaction to BDO proceeds, is in a range between 110 and 135° C.

In the case of the embodiment of the hydrogenation according to the invention of BYD to BDO in the stirred tank reactor operated in batchwise mode, a two-stage temperature regime is preferably selected. For this purpose, the temperature in the stirred tank at the start of the reaction is maintained in the range of 90 to 105° C. so that butyne-1,4-diol is reacted with hydrogen at least partially to give butene-1,4-diol. An ideal hold up time to the maximally complete conversion of BYD to butene-1,4-diol can be determined by detection of the amount of hydrogen taken up during this period. After uptake of the stoichiometric hydrogen equivalent to the amount of BYD used, the first reaction stage is concluded. The temperature in the stirred tank is then increased to 130 to 135° C. and maintained until completion of the hydrogenation to give 1,4-butanediol.

For an optimal reaction regime of the process according to the invention, the hydrogenation is carried out at a pH from 4.0 to 9.0.

Activated nickel catalysts are also fundamentally known to those skilled in the art as catalysts of the Raney type or basically "Raney nickel catalysts". They are generally prepared by forming an at least binary metal alloy, usually comprising aluminium (Al) and nickel (Ni), and subsequently leaching out aluminium.

The activated nickel catalysts used in the process according to the invention have a bulk density of not more than 0.8 kg/L, preferably from 0.1 to 0.7 kg/L, particularly preferably from 0.2 to 0.6 kg/L.

Bulk density $d_{Sch}$, sometimes also referred to as poured density of a solid, is the ratio of mass to volume of a mixture of a granular solid and air which fills the cavities between the particles. This parameter which is commonly used by those skilled in the art may be determined by means of a measuring cylinder by determining the mass ($M_F$) of a defined bed volume of solid ($V_F$):

$$d_{Sch}=M_F/V_F$$

The bulk density can be determined by slow addition of a defined amount of the drop-wet catalyst to a 1 L standard measuring cylinder filled with water. After settling of the catalyst is complete, the volume of the catalyst bed is read off the scale. The bulk density $d_{Sch}$, is calculated according to the equation $$d_{Sch}=M_F/V_F$$

where $M_F$ is the amount of catalyst used in the dry mass and $V_F$ is the volume of the bed observed under water. The dry mass of the activated catalyst can be determined by comparative weighing of a container of defined volume, which is filled with water and catalyst, to a container of the same volume, which is filled only with water. The mass of the dry catalyst is given by the difference of the two weights multiplied by a density factor k, which is derived from the quotient of the density of the dry catalyst and the difference in density between the dry catalyst and water. Density factors can be taken directly from the technical literature and/or the handling instructions of the manufacturers and distributors of catalysts of the Raney type and are typically about 1.2. The volume of the catalyst bed is directly accessible to those skilled in the art by reading off the scale of the measuring cylinder used. The method is independent of the particle size of the Raney type catalyst, i.e. independent of whether they are beds of granular or foam material or are powder catalysts under water.

The activated nickel catalysts used in the process according to the invention comprise 65 to 98% by weight, preferably 70 to 95% by weight, particularly preferably 80 to 90% by weight nickel and 0 to 15% by weight, preferably 0 to 13% by weight, particularly preferably 4 to 13% by weight, especially preferably 7 to 13% by weight aluminium. Furthermore, in preferred embodiments of the process according to the invention, activated nickel catalysts are used having up to 10% by weight, preferably 0.05 to 5% by weight, particularly preferably 0.1 to 2% by weight molybdenum (Mo) and/or 0 to 10% by weight, preferably 0.05 to 5% by weight, particularly preferably 1.5 to 3.5% by weight of one or more elements selected from the group consisting of iron and chromium.

The activated nickel catalysts used in the process according to the invention preferably have an average particle size of at most 70 mm. In principle, the optimal particle size is controllable and is matched to the conditions prevailing in the reactor used. The activated nickel catalysts are preferably used as loose material having a particle size of up to 50 mm, particularly preferably having a particle size of up to 30 mm and especially preferably of not more than 10 mm. The average particle size for the particles having a size in the range of 5 µm to 125 mm can be determined by sieve analysis according to DIN 66165. Alternatively, average particle size can be determined optically, by means of a microscope, in which a number average of at least 100 individual values should be determined.

The activated nickel catalysts used in the process according to the invention have a BET surface area of 1 to 200 m$^2$/g, preferably 10 to 120 m$^2$/g, particularly preferably 70 to 100 m$^2$/g. The specific surface area, also referred to as BET surface area for simplicity, is determined to DIN 9277 by nitrogen adsorption according to the Brunauer-Ernmett-Teller method as described in J. Am, Chem. Soc. 1938, Vol. 60, pp. 309-319.

The activated nickel catalysts used in the process according to the invention preferably have a macroscopic foam structure. Porous metal foam structures comprising many cavities may for example be formed by action of gases on a liquefied metal and subsequent cooling. A further option for achieving such structures is using organic foam structures as a template for the application of a metal and subsequently removing the organic template by incineration.

The activated nickel catalysts used in the process according to the invention preferably have a porous foam structure, wherein the macroscopic pores have sizes in the range of 200 to 2500 µm, particularly preferably 400 to 1200 µm. The size of the macroscopic pores may be determined using for example a method described in "The Guide 2000 of Technical Foams", book 4, part 4, pages 33-41. The size of the macroscopic pores may be determined by optical measurement of the pore diameter of a selected pore. This measurement is repeated for at least 100 different pores, and an average value of the pore diameter is then calculated therefrom as analysis result.

The invention further provides an activated nickel catalyst having a porous foam structure, wherein the macroscopic pores have sizes in the range of 100 to 5000 µm, and a bulk density of not more than 0.8 kg/L. In particular, this activated nickel catalyst can be used in a process for preparing 1,4-butanediol by hydrogenating 2-butyne-1,4-diol or 4-hydroxybutanal, wherein an aqueous solution comprising 2-butyne-1,4-diol or 4-hydroxybutanal is brought into contact with hydrogen and an activated nickel catalyst.

All the above definitions related to the catalysts used in the process according to the invention and illustrations related to the analytical methods correspondingly apply to the activated nickel catalysts according to the invention described below.

The activated nickel catalysts according to the invention have a bulk density of not more than 0.8 kg/L, preferably from 0.1 to 0.7 kg/L, particularly preferably from 0.2 to 0.6 kg/L. The activated nickel catalysts according to the invention comprise 65 to 98% by weight, preferably 70 to 95% by weight, particularly preferably 80 to 90% by weight nickel and 0 to 15% by weight, preferably 0 to 13% by weight, particularly preferably 4 to 13% by weight, especially preferably 7 to 13% by weight aluminium. Furthermore, preferred embodiments of the activated nickel catalysts according to the invention comprise up to 10% by weight, preferably 0.05 to 5% by weight, particularly preferably 0.1 to 2% by weight molybdenum (Mo) and/or 0 to 10% by weight, preferably 0.05 to 5% by weight, particularly preferably 1.5 to 3.5% by weight of one or more elements selected from the group consisting of iron and chromium.

The activated nickel catalysts according to the invention preferably have an average particle size of at most 70 mm. In principle, the optimal particle size is controllable and is matched to the conditions prevailing in the reactor used. The activated nickel catalysts according to the invention are preferably used as loose material having a particle size of up to 50 mm, particularly preferably having a particle size of up to 30 mm and especially preferably of not more than 10 mm.

The activated nickel catalysts according to the invention have a BET surface area of 1 to 200 m$^2$/g, preferably 10 to 120 m$^2$/g, particularly preferably 70 to 100 m$^2$/g.

The activated nickel catalysts according to the invention preferably have a macroscopic foam structure, wherein the macroscopic pores have sizes in the range of 200 to 2500 µm, particularly preferably 400 to 1200 µm.

To prepare an activated nickel catalyst according to the invention, a nickel metal foam is sprayed with an adhesion promoter, coated with aluminium powder and the material thus obtained is subjected to a heat treatment. Then a reduction, separation and/or shaping of the Ni/Al material obtained after the heat treatment is carried out. The activated nickel catalyst according to the invention is obtained therefrom by leaching out at least a portion of the aluminium contained therein.

The nickel metal foam to be used to prepare the catalyst according to the invention is preferably used in sheet form with edge lengths up to 500 mm and a thickness of not more than 5 mm. In order to improve the adhesion of aluminium powder to the nickel foam, this is initially treated with an adhesion promoter. Any adhesion promoter which improves adhesion between metals and organic materials may be employed. Polyethyleneimine solution for example is suitable.

After application of the aluminium powder to the nickel metal foam, the material is subjected to a heat treatment in the temperature range of 500 to 1000° C., preferably 600 to 800° C., wherein firstly moisture and organic residues from the aforementioned coating process are removed and subsequently aluminium is at least partially liquefied and is alloyed in the nickel foam structure. The heat treatment is effected in an atmosphere of oxygen-free inert gas to prevent formation of disruptive oxidic layers.

The material thus obtained, a nickel metal foam modified with aluminium, is then optionally comminuted, separated and/or subjected to an appropriate shaping. The comminution and separation of the nickel metal foam modified with aluminium may be effected, for example, by laser cutting or laser beam cutting. The resulting material pieces (particles) preferably have a cuboid or paralielepipedal shape having a maximum edge length of not more than 50 mm and form a bulk material in their totality.

In the next step, the catalyst according to the invention is obtained by activating the nickel foam modified with aluminium. For this purpose, at least a portion of the aluminium is chemically leached out of the material. For this purpose, aqueous basic solutions are used, preferably alkali metal hydroxide solutions selected from the group consisting of sodium hydroxide, potassium hydroxide or lithium hydroxide, particularly preferably aqueous sodium hydroxide solution. The concentration of the aqueous alkali metal hydroxide solution employed in the catalyst preparation can generally be between 0.1 and 60% by weight. The leaching out of the aluminium is preferably effected with a 5 to 50% by weight, particularly preferably 5 to 35% by weight, aqueous sodium hydroxide solution at a temperature of 20°

C. to 100° C., preferably at 40° C. to 85° C., particularly preferably at 50° C. to 80° C. The leaching times to be used here, that is the reaction times of the sodium hydroxide solution with the nickel metal foam modified with aluminium, depend on the aluminium content to be set in the end product, apart from the other reaction conditions mentioned above, and may be between 2 and 240 minutes.

In the activated nickel catalyst according to the invention generated as a result, the macroscopic foam structure of the nickel foam originally used is retained. The at least partial leaching out of the aluminum is effected in near-surface regions where a high-porosity, catalytically active nickel structure is generated. The BET surface area of the catalyst according to the invention is preferably greater than that of the nickel metal foam used.

To improve the activity, selectivity and/or service life of the activated nickel catalyst according to the invention, various dopants and/or promoters may be added. This may be effected by alloying a dopant metal in the nickel metal foam used in the catalyst preparation and/or by wet-chemical post-treatment of the activated nickel catalyst according to the invention. For example, the dopant metal can be applied by precipitation or reductive decomposition from preferably aqueous solution of a suitable precursor. One or more dopant elements are preferably applied, selected from the group consisting of platinum (Pt), palladium (Pd), rhodium (Rh), ruthenium (Ru), osmium (Os), iridium (Ir), iron (Fe), cobalt (Co), chromium (Cr), molybdenum (Mo), tungsten (Wo), manganese (Mn), rhenium (Re), copper (Cu), silver (Ag) and gold (Au). Particular preference is given to Fe, Co, Cr and/or Mo.

The invention is more particularly elucidated herein below with reference to some examples and figures.

EXAMPLE 1

A nickel foam commercially available in rolls and having a thickness of 1.9 mm, a width of 300 mm and an average pore size of 580 µm was sprayed with a commercially available adhesion promoter solution, coated with aluminium powder and subjected to a heat treatment at 700° C. After cooling the material thus obtained was cut with a laser into square pieces having an edge length of 4 mm×4 mm and a thickness of 1.9 mm.

The resulting loose material was arranged in a fixed bed for the catalytic activation and subsequently wet-chemically treated by pumping through 5M NaOH solution (aqueous sodium hydroxide solution). A portion A of the loose material was subjected to this wet-chemical post-treatment at 70° C. for a period of 5 minutes. A portion B of the loose material was post-treated at 60° C. with aqueous sodium hydroxide solution for a period of 15 minutes.

Both portions were subsequently washed with water until a pH<10 of the wash solution after pumping through the fixed bed had been reached.

The composition of the two catalytically active loose material portions thus obtained was analysed by ICP-OES. The results are compiled in the following table:

| Catalyst | Nickel content | Aluminium content | Bulk density |
|---|---|---|---|
| A | 85.8 wt % | 14.1 wt % | 0.5 kg/L |
| B | 85.3 wt % | 14.7 wt % | 0.5 kg/L |

The bulk densities specified in the table above were determined by slow addition of a defined amount of the drop-wet catalyst to a 1 L standard measuring cylinder filled with water. After settling of the catalyst is complete, the volume of the catalyst bed is read off the scale. The bulk density $d_{Sch}$ is calculated according to the equation $$d_{Sch} = M_F / V_F$$

where $M_F$ is the amount of catalyst used in the dry mass and $V_F$ is the volume of the bed observed under water. The dry mass of the activated catalyst is determined by comparative weighing of a container of defined volume, which is filled with water and catalyst, to a container of the same volume, which is filled only with water. The mass of the dry catalyst is given by the difference of the two weights multiplied by a density factor k, which is derived from the quotient of the density of the dry catalyst and the difference in density between the thy catalyst and water. Density factors can be taken directly from the technical literature and/or the handling instructions of the manufacturers and distributors of catalysts of the Raney type and are typically about 1.2. The volume of the catalyst bed is directly accessible to those skilled in the art by reading off the scale of the measuring cylinder used. The method is independent of the particle size of the Raney type catalyst, i.e. independent of whether they are beds of granular or foam material or are powder catalysts under water.

Catalyst A was introduced into a stirred tank reactor with a total volume of 500 ml in order to investigate the catalytic efficacy in the hydrogenation of butyne-1,4-diol (BYD) to 1,4-butynediol (BDO). 300 mL of water were initially charged in the reactor, 5 mL of catalyst A were introduced 2.0 into a basket positioned below the water level close to the stirring shaft. After closing the reactor, atmosphere exchange and filling the reactor with hydrogen up to a pressure of 80 bar, 86.6 g of BYD in 50% aqueous solution were pumped into the reactor with stirring and the reactor was heated to 100° C. After a reaction time of 100 minutes, the temperature in the reactor was increased to 135° C. and maintained for a further 260 minutes. After cooling to room temperature, a sample of the reaction mixture was removed and analysed by gas chromatography. From the measured concentrations of the constituents of the reaction mixture, the butynediol conversion, the yield to give BDO and the selectivity for BDO, and also the space-time yield $STY_{BDO,V}$ based on the catalyst volume were determined. The results are compiled in the following table:

| BYD conversion | Yield of BDO | Selectivity for BDO | $STY_{BDO,V}$ |
|---|---|---|---|
| 97% | 86% | 89% | 1.30 kg/(L cat*h) |

The quantities stated are calculated as follows:
BYD conversion is defined as the molar amount of BYD consumed based on the molar amount of BYD used:

$$U_{BYD}[\%] = \frac{n_0(BYD) - n(BYD)}{n_0(BYD)} * 100,$$

where $n_0$ (BYD)=molar amount of BYD used and
$n$ (BYD)=molar amount of BYD at the end of the reaction
yield of BDO is defined as the molar amount of BDO obtained based on the molar amount of BYD used:

$$Y_{BDO}[\%] = \frac{n(BDO)}{n_0(BYD)} * 100$$

selectivity for BDO is defined as the ratio of the amount of desired product BDO formed to the amount of reactant BYD converted:

$$S_{BDO}[\%] = \frac{n(BDO)}{n_0(BYD) - n(BYD)} * 100$$

the catalyst volume-based space-time yield is defined as the production output based on the volume of catalyst (in litres), where production output is understood to mean the mass of desired BDO product (in kg) generated per reaction run based on the reaction time t (in hours $$STY_{BDO,V} = \frac{m(BDO)}{V_{cat} * t}$$

EXAMPLE 2

A catalyst was prepared as described in example 1, wherein the wet-chemical post-treatment was carried out with 10% by weight aqueous sodium hydroxide solution at 60° C. for a period of 60 minutes. Analysis by ICP-OES gave a composition of the resulting catalytically active bulk material (catalyst C) of 89% by weight nickel and 11% by weight aluminium. The material had a bulk density of $d_{Sch}$=0.3 kg/L. The bulk density was determined according to the procedure described in example 1.

Catalyst C was also investigated for its catalytic efficacy in the hydrogenation of butyne-1,4-diol (BYD) to 1,4-butanediol (BDO) in a stirred tank reactor. Experimental setup, procedure and evaluation were carried out as described in example 1.

The results are compiled in the following table:

| BYD conversion | Yield of BDO | Selectivity for BDO | $STY_{BDO,V}$ |
|---|---|---|---|
| 97% | 90% | 93% | 1.37 kg/(L cat*h) |

From the bulk density of catalyst C and the catalyst volume-based space-time yield, the space-time yield $STY_{BDO,m}$ based on the catalyst mass could be calculated as follows:

$$STY_{BDO,m} = STY_{BDO,V}/d_{Sch}$$

It was $STY_{BDO,m}$=4.55 kg/(kg cat*h).

EXAMPLE 3

A catalyst was prepared as described in example 1, wherein the wet-chemical post-treatment was carried out with 10% by weight aqueous sodium hydroxide solution at 80° C. for a period of 90 minutes. After completion of the wet-chemical treatment with aqueous sodium hydroxide solution, molybdenum was precipitated on the catalyst from an aqueous molybdate solution. Analysis by ICP-OES gave a composition of the resulting catalytically active bulk material (catalyst 0) of 91% by weight nickel, 8.7% by weight aluminium and 0.3% by weight molybdenum. The material had a bulk density of $d_{Sch}$=0.32 kg/L. The bulk density was determined according to the procedure described in example 1.

Catalyst D was used in a pilot fixed bed reactor for the hydrogenation of 4-hydroxybutanal (HBA) to BDO at a temperature of 60° C. and a hydrogen pressure of 100 bar and showed virtually quantitative HBA conversion with very good BDO yields and selectivities for BDO.

COMPARATIVE EXAMPLE

An activated nickel catalyst of the granulate type was prepared, as known from the prior art, e.g. DE 2004611A, and used in customary industrial plants for preparing BDO. To this end, by melting nickel and aluminum, an alloy consisting of 42% by weight nickel and 58% by weight aluminum was produced, subjected to mechanical comminution and sieved to obtain a grain fraction having a particle size of 1.8 to 4 mm. This alloy pellet fraction was catalytically activated in a loose fill fixed bed by pumping a 10% by weight aqueous sodium hydroxide solution therethrough at 60° C. for a duration of 60 minutes and subsequently washing with water until a pH of the resulting washing solution of <10 had been achieved. The resulting catalyst had a bulk density of $d_{Sch}$=1.7 kg/L. The bulk density was determined according to the procedure described in example 1. The aluminium content was approximately 37% by weight aluminium.

This catalyst according to the prior art was also investigated for its catalytic efficacy in the hydrogenation of butyne-1,4-diol (BYD) to 1,4-butanediol (BDO) in a stirred tank reactor. Experimental setup, procedure and evaluation were carried out as described in example 1. The results are compiled in the following table:

| BYD conversion | Yield of BDO | Selectivity for BDO | $STY_{BDO,V}$ |
|---|---|---|---|
| 97% | 85% | 88% | 1.29 kg/(L cat*h) |

From the bulk density of the catalyst according to the prior art and the catalyst volume-based space-time yield, the space-time yield $STY_{BDO,m}$ based on the catalyst mass could be calculated. It was 0.75 kg/(kg cat*h).

The results obtained in the stirred tank experiments for the catalysts A (from example 1) and C (from example 2) are compared with the characteristics obtained using the catalyst according to the prior art (comparative example): at constant conversion, catalyst A shows a slight improvement, catalyst C shows a considerable improvement in BDO yield and selectivity for BDO.

Also, the space-time yields based on the catalyst mass which were achieved using the catalyst of the granulate type according to the prior art (comparative example) and the inventive catalyst C are compared. Clearly recognizable is a six-fold increase in the value for inventive catalyst C compared to the prior art.

The resultant amounts saved of nickel for an industrial fixed bed reactor is calculated below as an example of a typical BDO reactor comprising 20 m³ of catalyst bed.

In around-the-clock continuous operating mode, such a plant is operated productively on average for at least 8000 operating hours per year. At a catalyst volume-based space-time yield of 1.29 kg/(L cat*h)=1.29 t/(m³ cat*h) for the nickel catalyst of the granulate type according to the prior art (comparative example), an annual amount of BDO produced results therefrom of 1.29×20×8000 t=206400 t of BDO. Using the catalyst according to the prior art, which has a bulk density of 1.7 kg/L=1.7 t/m³ at a nickel content of 60-65% by weight, at least 20×1.7×0.6 t=20.4 t of nickel are required therefor.

In order to produce the same amount of BDO over catalyst C of example 2, which has a catalyst volume-based space-time yield of 1.37 kg/(L cat*h)=1.37 t/(m³ cat*h), 206400/ (1.37*8000) m³ 18.83 m³ of catalyst are required. This corresponds to a catalyst volume saving of 1.17 m³ of catalyst or 5.85%. The amount of catalyst C required at a bulk density of inventive catalyst C of 0.3 kg/L=0.3 t/m³ is 18.83×0.3 t=5.649 t of catalyst C. This corresponds at a nickel content of 89% by weight to a nickel requirement of 5 t compared to a nickel requirement of at least 20.4 t using catalyst of the granulate type according to the prior art.

Therefore, the amount of nickel required can be reduced to ¼ of the current usual amount by means of the process according to the invention, by which means an extremely efficient process for 2.0 preparing 1,4-butanediol is provided.

The invention claimed is:

1. A process for preparing 1,4-butanediol by hydrogenating 2-butyne-1,4-diol or 4-hydroxybutanal, said method comprising contacting an aqueous solution comprising 2-butyne-1,4-diol or 4-hydroxybutanal with hydrogen and an activated nickel catalyst, wherein said activated nickel catalyst comprises:
   a) a porous foam structure;
   b) macroscopic pores in the range of 100 to 5000 μm;
   c) a bulk density of not more than 0.8 kg/L.

2. The process of claim 1, wherein the hydrogenation of 4-hydroxybutanal is carried out at a hydrogen pressure in the range of 10 to 110 bar.

3. The process of claim 2, wherein the hydrogenation is carried out in a temperature range of 50 to 200° C.

4. The process of claim 1, wherein the hydrogenation of 2-butyne-1,4-diol is carried out at a hydrogen pressure in the range of 50 to 350 bar and a temperature range of 50 to 150° C.

5. The process of claim 1, wherein said process is carried out in a fixed bed reactor.

6. The process of claim 5, wherein the fixed bed reactor is operated adiabatically, with a temperature at the reactor inlet in the range of 80 to 100° C. and a temperature at the reactor outlet in the range of 110 to 150° C.

7. The process of claim 6, wherein the activated nickel catalyst has an aluminum content of not more than 15% by weight.

8. The process of claim 7, wherein the activated nickel catalyst comprises macroscopic pores with sizes in the range of 200 to 2500 μm.

9. The process of claim 5, wherein the process is carried out continuously in a trickle bed reactor, liquid-filled reactor, or a bubble column.

10. The method of claim 5, wherein the fixed bed reactor is operated in a "once through" mode, in which the reactants are introduced into the reactor and the product mixture is removed after the reaction.

11. The process of claim 1, wherein the activated nickel catalyst comprises 0 to 10% by weight of at least one of the elements selected from the group consisting of: molybdenum, iron, and chromium.

12. The process of claim 11, wherein the hydrogenation is carried out continuously.

13. The process of claim 12, wherein the activated nickel catalyst has an aluminum content of not more than 15% by weight.

14. The process of claim 13, wherein the activated nickel catalyst has a porous foam structure, wherein the macroscopic pores have sizes in the range of 200 to 2500 μm.

15. The process of claim 1, wherein the hydrogenation is carried out batchwise in a stirred tank reactor using a two temperature reaction regime, wherein:
   a) the temperature in the stirred tank at the start of the reaction is maintained in the range of 90 to 105° C. so that 2-butyne-1,4-diol is reacted with hydrogen to give 2-butene-1,4-diol;
   b) after uptake of hydrogen stoichiometrically equivalent to the amount of 2-butyne-1,4-diol used, the first reaction stage is concluded and the temperature in the stirred tank is then increased to 130 to 135° C. and maintained in that range until completion of the hydrogenation to give 1,4-butanediol.

16. The process of claim 15, wherein the catalyst is arranged in a holding device close to the stirrer shaft such that a flow of the reaction mixture through the catalyst bed is generated by the stirrer.

17. The process of claim 15, wherein the hydrogenation of butyne-1,4-diol is carried out at a hydrogen pressure in the range of 50 to 350 bar.

18. The process of claim 17, wherein the activated nickel catalyst has an aluminum content of not more than 15% by weight.

19. The process of claim 15, wherein the activated nickel catalyst comprises macroscopic pores with sizes in the range of 200 to 2500 μm.

20. The process of claim 15, wherein the activated nickel catalyst comprises 0 to 10% by weight of at least one of the elements selected from the group consisting of: molybdenum, iron, and chromium.

* * * * *